(12) United States Patent
Zhou

(10) Patent No.: US 10,758,586 B2
(45) Date of Patent: Sep. 1, 2020

(54) COMPOSITION CONTAINING RHIZOMA POLYGONATI AND HAVING A HEALTH PRESERVING EFFECT

(71) Applicant: Ran Zhou, Shanxi (CN)

(72) Inventor: Ran Zhou, Shanxi (CN)

( * ) Notice: Subject to any disclaimer, the term of this patent is extended or adjusted under 35 U.S.C. 154(b) by 0 days.

(21) Appl. No.: 16/326,996

(22) PCT Filed: Mar. 19, 2018

(86) PCT No.: PCT/CN2018/079417
§ 371 (c)(1),
(2) Date: Feb. 21, 2019

(87) PCT Pub. No.: WO2018/192329
PCT Pub. Date: Oct. 25, 2018

(65) Prior Publication Data
US 2019/0175682 A1    Jun. 13, 2019

(30) Foreign Application Priority Data
Apr. 17, 2017 (CN) .......................... 2017 1 0250791

(51) Int. Cl.
| | |
|---|---|
| *A61K 36/8969* | (2006.01) |
| *C12G 1/00* | (2019.01) |
| *A61P 37/04* | (2006.01) |
| *C12G 3/04* | (2019.01) |
| *C12G 3/02* | (2019.01) |

(52) U.S. Cl.
CPC .......... *A61K 36/8969* (2013.01); *A61P 37/04* (2018.01); *C12G 1/00* (2013.01); *C12G 3/02* (2013.01); *C12G 3/04* (2013.01); *A61K 2236/00* (2013.01); *C12G 2200/21* (2013.01); *Y02P 60/873* (2015.11)

(58) Field of Classification Search
None
See application file for complete search history.

(56) References Cited

FOREIGN PATENT DOCUMENTS

| | | | |
|---|---|---|---|
| CN | 103865717 A | * | 6/2014 |
| CN | 103865720 A | | 6/2014 |
| CN | 104789409 A | * | 7/2015 |
| CN | 107083309 A | | 8/2017 |

OTHER PUBLICATIONS

International Search Report and Written Opinion dated Jun. 8, 2018 in corresponding International Patent Application No. PCT/CN2018/079417.
Chinese Office Action from counterpart Chinese Patent Application No. 2017102507917, dated Feb. 25, 2020.
Australian Examination Report from counterpart Australian Patent Application No. 201825557, dated Mar. 6, 2020.
Jin Kong, et al., "Development and Research of Nourishing Foods Prepared from Polygonatum Sibiricum Red.," The Journal of Food Study and Development, vol. 20, No. 4, pp. 34-36, Dec. 1998.

* cited by examiner

*Primary Examiner* — Ralph J Gitomer
(74) *Attorney, Agent, or Firm* — Miles & Stockbridge P.C.; Ajay Jagtiani

(57) ABSTRACT

A composition with a health preserving effect, comprising 2.5-6.5 parts of Rhizoma Polygonati and 27.5-84.5 parts of a Rhizoma Polygonati-soaked solution mixture. The Rhizoma Polygonati-soaked solution mixture is a mixture of a baijiu soaking solution obtained by soaking Rhizoma Polygonati in baijiu and dregs of a decoction. Also provided are health preserving wine prepared from the composition and a preparation method thereof. The preparation method comprises subjecting the Rhizoma Polygonati and the Rhizoma Polygonati-soaked solution mixture to mixed culture fermentation with proso millet. The health preserving wine is prepared by combining fermentation and soaking processes.

7 Claims, No Drawings

COMPOSITION CONTAINING RHIZOMA POLYGONATI AND HAVING A HEALTH PRESERVING EFFECT

TECHNICAL FIELD

The application belongs to the technical field of wine used for drinking, and particularly relates to a composition with a health preserving effect, a health preserving wine prepared therefrom and a preparation method and application of the health preserving wine.

BACKGROUND

Wine culture has a long history in China, and the types of wine has also developed rapidly with the advancement of technique for making wine. Moderate drinking is good for health. There has been a saying that "wine is a leader for all medicine" since ancient times. In addition to alcohol, wine also comprises nutrients such as organic acids, amino acids, esters, sugars, higher alcohols and less vitamins and indeed, wine is beneficial for health. It is believed that wine itself is a medicine in Traditional Chinese Medicine, and it can also be used to cure diseases. Wine is the nutritional substance from water and grain, which tastes sweet and pungent, easy to stimulates organs of human and has an effect mainly on heart and liver. Wine has the following effects: clearing blood vessels, activating blood circulation, removing phlegm, dispersing pathogenic cold and eliminating cold, treating coagulated cold by purgation, removing stomach cold, nourishing spleen, thickening the stomach and intestines, promoting digestion and moistening skin, and wine can lead drugs to go up to the upper limb and enhance the effects of drugs. Therefore, the combination of wine and traditional medicine, i.e. medicinal wine, is very popular. The medicinal wine is also called health preserving wine. The medicine comprised therein is traditional Chinese medicine generally deriving from animal and plant and having less side effects. The wine is baijiu or yellow wine. The combination of the two increases the effects of the wine and the delivery of the medicine such that the combination on the one hand contains the characteristics of medicine, and on the other hand maintains the characteristics of wine, which makes the combination between food and medicine. It can cure disease and keep a healthy body with a good therapeutic and health preserving effect.

With the improvement of people's living standards, the awareness of preserving health has gradually increased, and medicinal wine has become more and more valued and loved by people. At present, Chinese medicinal wine has been expanded to overseas and become favored by the whole world. However, most of the medicinal wine on the market are made by soaking and blending. The taste and coordination are poor, less elegant and delicate.

To solve this problem, Chinese patent application document CN103865720A discloses a health preserving wine comprising Rhizoma Polygonati and *Astragalus membranaceus* and a preparation method thereof. This health preserving wine is obtained by a traditional yellow wine brewing technology using proso millet, *Astragalus membranaceus*, Rhizoma Polygonati, daqu and yeast as raw materials. The traditional yellow wine brewing technology comprises soaking, cooking and cooling the proso millet, stirring and mixing with other raw materials, putting them in a tank for fermentation, then pressing the mixture to obtain a filter solution and clarifying the filter solution, and boiling the filter solution for sterilization, obtaining a new type of tonifying alcoholic beverage with harmonious fragrance, pleasant taste and low alcohol content. However, one of the raw materials used in the above-mentioned health preserving wine, *Astragalus membranaceus*, is a traditional Chinese medicine with strong tonifying property. Its efficacy of benefiting vital energy for consolidating superficies is very strong. People who do not have spleen and stomach weakness are not suitable for drinking a health preserving wine containing *Astragalus membranaceus*, and after drinking this wine, they will feel discomfort obviously especially in summer, and the feeling mainly manifested as the symptoms of developing inflammatory. However, if *Astragalus membranaceus* is simply omitted in the above-mentioned raw materials, the health preserving effect will decrease. Therefore, it is of great significance to prepare a health preserving wine suitable for people who do not have spleen and stomach weakness and all people by changing the preparation process without decreasing the efficacy of the existing health preserving wine.

SUMMARY OF THE INVENTION

Therefore, the technical problem to be solved by the present application is how to overcome the defect that the health preserving wine prepared by using *Astragalus membranaceus* as one of the raw materials in the prior art is not suitable for people who don't have the spleen and stomach weakness, and further the present application provides a health preserving wine recipe not using *Astragalus membranaceus* as raw material without decreasing the efficacy and a preparation method of the health preserving wine.

For this purpose, the technical solution of the present application is as follows:

The present application provides a composition with a health preserving effect, comprising the following parts by weight of raw materials:

2.5-6.5 parts by weight of Rhizoma Polygonati, and 27.5 to 84.5 parts by weight of a Rhizoma Polygonati-soaked solution mixture;

wherein the Rhizoma Polygonati-soaked solution mixture is a mixture of a baijiu soaking solution and dregs obtained by soaking Rhizoma Polygonati in baijiu.

Optionally, the Rhizoma Polygonati-soaked solution mixture is obtained by soaking 2.5 to 6.5 parts by weight of Rhizoma Polygonati in 25.0 to 78.0 parts by weight of baijiu and wherein baijiu has an alcohol content by volume of 55% to 65%.

Optionally, the soaking lasts for 30 to 60 days.

The present application also provides a health product with a health preserving effect prepared with the above mentioned composition.

The present application also provides a health preserving wine with a health preserving effect prepared with the above mentioned composition.

Optionally, the health preserving wine prepared with the above mentioned composition of the present application comprises the following parts by weight of raw materials:

2.5 to 6.5 parts by weight of Rhizoma Polygonati;

27.5 to 84.5 parts by weight of a Rhizoma Polygonati-soaked solution mixture;

77.0 to 85.0 parts by weight of proso millet;

9.9 parts by weight of daqu; and 0.1 parts by weight of yeast

The present application provides a method for preparing a health preserving wine, comprising the following steps:

(1) soaking 2.5 to 6.5 parts by weight of Rhizoma Polygonati in 25.0 to 78.0 parts by weight of baijiu to obtain 27.5 to 84.5 parts by weight of a Rhizoma Polygonati-soaked solution mixture, wherein baijiu has an alcohol content by volume of 55% to 65%.

(2) subjecting 77.0 to 85.0 parts by weight of proso millet to soaking and cooking to obtain a cooked proso millet;

(3) cooling the cooked proso millet obtained in step (2) to a temperature of 24° C. to 26° C., then adding it to a fermentation tank, adding water and 9.9 parts by weight of daqu, 0.1 parts by weight of yeast and 2.5 to 6.5 parts by weight of Rhizoma Polygonati, fermenting at 25° C. to 30° C. for 3 to 5 days, then adding baijiu and 27.5 to 84.5 parts by weight of the Rhizoma Polygonati-soaked solution mixture obtained in step (1), and further fermenting at 18° C. to 22° C. for 50 to 60 days to prepare a mash;

(4) pressing the mash obtained in step (3) to obtain a pressed mash, filtering the pressed mash to obtain a wine liquid and a vinasse, allowing the wine liquid to stand for 2 to 3 days at 5° C. to 15° C. to obtain a supernatant, filtering the supernatant to prepare a raw wine;

(5) sterilizing the raw wine obtained in step (4) at 70 to 90° C. for 10 to 30 minutes, then aging for at least 1 year to produce an aged wine;

(6) adding pure water to the aged wine obtained in step (5) to adjust alcohol content to 15% to 21% by volume, then adding a white sugar and/or a crystal sugar to adjust sugar degree to 3 to 10°, finally adding a caramel pigment to adjust the color, thereby obtaining a semi-finished wine;

(7) filling the semi-finished wine obtained in step (6) and sterilizing at 70° C. to 90° C. for 10 to 30 minutes, then packing and storing to make a health preserving wine.

Optionally, the soaking in step (1) is carried out at a temperature of 10° C. to 25° C.

Optionally, the cooked proso millet in step (2) is obtained by soaking the proso millet in water for 2 to 3 days, and cooking for 15 to 25 minutes at a temperature of 75° C. to 90° C.

Optionally, in step (3) an adding amount of water is 2 to 3 times a weight of the cooked proso millet, and an adding amount of the baijiu is 40% to 60% of the weight of the cooked proso millet.

Optionally, in step (4) said filtering the pressed mash is carried out with a filter cloth made of nylon 36, and said filtering the supernatant is carried out with a filter cloth made of nylon 36.

The application also provides the use of the above mentioned composition with a health preserving effect in a method for enhancing immune function.

The technical solution of the application has the following advantages:

1. The present application provides a composition with a health preserving effect. The composition comprises Rhizoma Polygonati and a mixture obtained by soaking Rhizoma Polygonati in baijiu. In the composition of the application, Rhizoma Polygonati tastes sweet, the efficacy is moderate and not strong, and Rhizoma Polygonati has an effect mainly on spleen, lung and kidney, while coordinating a visceral, and tonifying the kidney and improving the immune function. Rhizoma Polygonati is soaked in baijiu for a long time to obtain the Rhizoma Polygonati soaked solution mixture. The process of soaking allows the active ingredients of Rhizoma Polygonati to blend into baijiu. The combination of Rhizoma Polygonati and baijiu makes the composition have a better health preserving effect.

2. The present application also provides a health preserving wine prepared by mixing above-mentioned composition having a health preserving effect with proso millet, Daqu, and yeast and fermenting the mixture.

Proso millet is a main raw material for making yellow wine in northern China. Proso millet has the following advantages: Firstly, proso millet contains relatively high content of starch and relatively low content of other components such as protein, which result in off-flavor in the wine. Secondly, the starch contained in the proso millet is almost all amylopectin, which absorbs water quickly, is easy to be cooked and gelatinized, and is not easily to be broken down by starch glucoamylase, so that more dextrins and oligosaccharides remain in the wine, and the resulted wine tastes sweet and mellow. Adding 77.0. to 85.0 parts by weight of proso millet ensures the health preserving wine tastes better with better coordination.

The unprocessed mixture of Rhizoma Polygonati and Rhizoma Polygonati soaked solution are mixed together for fermentation, so that more active ingredients of Rhizoma Polygonati are dissolved into baijiu, and thus the health preserving effect of the health preserving wine is enhanced. In particular, compared with the existing health preserving wines prepared by fermentation of only Rhizoma Polygonati and *Astragalus membranaceus*, the health preserving wine of the application completely avoids the adverse effects brought by the *Astragalus membranaceus* (because *Astragalus membranaceus* has a strong tonifying effect, people who do not have spleen and stomach weakness are not suitable for drinking a health preserving wine containing *Astragalus membranaceus*, and after drinking this wine, they will feel discomfort obviously especially in summer, and the feeling mainly manifested as the symptoms of developing inflammatory). It is more suitable for people who do not have spleen and stomach weakness, and the effect of the health preserving wine of the present application is no less than the existing health preserving wine. Therefore, the present wine can be used as a health preserving product for subhealthy people nowadays.

3. The present application also provides a preparation method of the health preserving wine, comprising the following steps: firstly soaking a part of Rhizoma Polygonati in baijiu, so that the active ingredients of Rhizoma Polygonati is dissolved into baijiu; and then adopting the traditional rice wine brewing process so as to fully taking advantage of the proso millet for brewing the rice wine, comprising: soaking, cooking and cooling the rice, mixing the cooked rice, putting them in a tank, then adding Rhizoma Polygonati-soaked solution mixture and another part of Rhizoma Polygonati to the proso millet in a certain proportion, and adding a certain amount of the Daqu and the yeast for fermentation, then pressing the mixture to obtain a filter solution and clarifying the filter solution, and boiling the filter solution for sterilization. The fermentation process ensures the harmony and softness tastes of the health preserving wine. It is particularly noted that the soaking and fermentation processes are organically combined in the present application so that the dissolution rate of the active ingredients of Rhizoma Polygonati is greatly improved, and the efficacy of Rhizoma Polygonati is maximized.

4. In the preparation process of the health preserving wine provided by the application, the vinasse can be used to prepare fodder after being dried, so that the utilization rate is improved, and the cost of the health preserving wine is reduced.

DETAILED DESCRIPTION

In order to promote the understanding of the object, technical solutions and gist of the present application, the embodiments of the present application will be described in further detail below. The application may be performed in many different forms and should not be construed as being limited to the examples set forth herein. Rather, the examples are provided to illustrate the present application and fully convey the concept of the present application to those skilled in the art. The present application is to be construed as being limited by the claims.

Example 1

The present application provides a health preserving wine, comprising the following parts by weight of raw materials:

4.5 parts by weight of Rhizoma Polygonati; 56.0 parts by weight of a Rhizoma Polygonati-soaked solution mixture; 81.0 parts by weight of proso millet; 9.9 parts by weight of Daqu; and 0.1 parts by weight of yeast.

Among them, the Rhizoma Polygonati-soaked solution mixture is a mixture of baijiu soaking solution and dregs obtained by soaking 4.5 parts by weight of Rhizoma Polygonati in 51.5 parts by weight of baijiu, so the mixture is of 56.0 parts by weight in total. The baijiu used herein has an alcohol content of 60% by volume, and the soaking last for 45 days.

The present application provides a preparation method of a health preserving wine prepared by using the above raw materials, comprising the following steps:

(1) soaking 4.5 parts by weight of Rhizoma Polygonati in 51.5 parts by weight of baijiu with an alcohol content of 60% by volume at a temperature of 16° C. for 45 days to obtain a mixture of baijiu soaking solution of Rhizoma Polygonati and dregs, i.e., Rhizoma Polygonati-soaked solution mixture of 56.0 parts by weight;

(2) subjecting 81.0 parts by weight of proso millet to soaking in water for 2.5 days and then cooking at 83° C. for 20 minutes to obtain a cooked proso millet;

(3) cooling the cooked proso millet obtained in step (2) to 25° C., then adding it to a fermentation tank, adding water and 9.9 parts by weight of daqu, 0.1 parts by weight of yeast and 4.5 parts by weight of Rhizoma Polygonati, fermenting at 28° C. for 4 days, then adding baijiu and 56.0 parts by weight of Rhizoma Polygonati-soaked solution mixture obtained in step (1), and further fermenting at 20° C. for 55 days to prepare a mash, wherein the adding amount of water is 2.5 times the weight of the cooked proso millet, and the adding amount of baijiu is 50% of the weight of the cooked proso millet;

(4) pressing the mash obtained in step (3) to obtain a pressed mash, filtering the pressed mash to obtain a wine liquid and a vinasse, s allowing the wine liquid to stand for 2.5 days at 10° C. to obtain a supernatant, filtering the supernatant to prepare a raw wine, wherein a filter cloth made of nylon 36 is used in all of the above filtering;

(5) sterilizing the raw wine obtained in step (4) at 80° C. for 20 minutes, then aging for 2 years to produce an aged wine;

(6) adding pure water to the aged wine obtained in step (5) to adjust alcohol content to 18% by volume, then adding a white sugar to adjust sugar degree to 6°, finally adding a caramel pigment to adjust the color, thereby obtaining a semi-finished wine;

(7) filling the semi-finished wine obtained step (6) and sterilizing at 80° C. for 20 minutes, then packing and storing to make a health preserving wine.

Example 2

The present application provides a health preserving wine comprising the following parts by weight of raw materials:

2.5 parts by weight of Rhizoma Polygonati; 27.5 parts by weight of a Rhizoma Polygonati-soaked solution mixture; 85.0 parts by weight of proso millet; 9.9 parts by weight of Daqu; and 0.1 parts by weight of yeast.

Among them, the Rhizoma Polygonati-soaked solution mixture is a mixture of baijiu soaking solution and dregs obtained by soaking 2.5 parts by weight of Rhizoma Polygonati in 25.0 parts by weight of baijiu, and the mixture is of 27.5 parts by weight in total. The baijiu used herein has an alcohol content of 55% by volume and the soaking lasts for 60 days.

The present application provides a preparation method of a health preserving wine prepared by using the above raw materials, comprising the following steps:

(1) soaking 2.5 parts by weight of Rhizoma Polygonati in 25.0 parts by weight of baijiu with an alcohol content of 55% by volume at a temperature of 25° C. for 60 days to obtain a mixture of baijiu soaking solution of Rhizoma Polygonati and dregs, i.e., Rhizoma Polygonati-soaked solution mixture of 27.5 parts by weight;

(2) subjecting 85.0 parts by weight of proso millet to soaking in water for 2 days and then cooking at 90° C. for 15 minutes to obtain a cooked proso millet;

(3) cooling the cooked proso millet obtained in step (2) to 26° C., then adding it to a fermentation tank, adding water and 9.9 parts by weight of daqu, 0.1 parts by weight of yeast and 2.5 parts by weight of Rhizoma Polygonati, fermenting at 25° C. for 5 days, then adding baijiu and 27.5 parts by weight of the Rhizoma Polygonati-soaked solution mixture obtained in step (1), and further fermenting at 22° C. for 50 days to prepare a mash, wherein the adding amount of water is 3 times the weight of the cooked proso millet, and the adding amount of baijiu is 40% of the weight of the cooked proso millet;

(4) pressing the mash obtained in step (3) and filtering the pressed mash to obtain a wine liquid and a vinasse, allowing the wine liquid to stand for 2 days at 15° C. to obtain a supernatant, filtering the supernatant to prepare a raw wine, wherein a filter cloth made of nylon 36 is used in all of the above filtering;

(5) sterilizing the raw wine obtained in step (4) at 90° C. for 10 minutes, then aging for 1 year to produce an aged wine;

(6) adding pure water to the aged wine obtained in step (5) to adjust alcohol content to 15% by volume, then adding a white sugar to adjust sugar degree to 10°, finally adding a caramel pigment to adjust the color, thereby obtaining a semi-finished wine;

(7) filling the semi-finished wine obtained in step (6) and sterilizing at 70° C. for 30 minutes, then packing and storing to make a health preserving wine.

Example 3

The present application provides a health preserving wine, comprising the following parts by weight of raw materials:

6.5 parts by weight of Rhizoma Polygonati; 84.5 parts by weight of a Rhizoma Polygonati-soaked solution mixture; 77.0 parts by weight of the proso millet; 9.9 parts by weight of Daqu; and 0.1 parts by weight of yeast.

Among them, the Rhizoma Polygonati-soaked solution mixture is a mixture of baijiu soaking solution and dregs obtained by soaking 6.5 parts by weight of Rhizoma Polygonati in 78.0 parts by weight of baijiu, and the mixture is of 84.5 parts by weight in total, wherein the baijiu herein used has an alcohol content of 65% by volume and the soaking lasts for 30 days.

The present application provides a method of preparing a health preserving wine prepared with the above raw materials, comprising the following steps:

(1) soaking 6.5 parts by weight of Rhizoma Polygonati in 78.0 parts by weight of baijiu with an alcohol content of 65% by volume at a temperature of 10° C. for 30 days to obtain a mixture of baijiu soaking solution of Rhizoma Polygonati and dregs, i.e., Rhizoma Polygonati-soaked solution mixture of 84.5 parts by weight;

(2) subjecting 77.0 parts by weight of proso millet to soaking in water for 3 days and then cooking at 75° C. for 25 minutes to obtain a cooked proso millet;

(3) cooling the cooked proso millet obtained in step (2) to 24° C., then adding it to a fermentation tank, adding water and 9.9 parts by weight of daqu, 0.1 parts by weight of yeast and 6.5 parts by weight of Rhizoma Polygonati, fermenting at 30° C. for 3 days, then adding baijiu and 84.5 parts by weight of the Rhizoma Polygonati-soaked solution mixture obtained in step (1), and further fermenting at 18° C. for 60 days to prepare a mash, wherein the adding amount of water is 2 times the weight of the cooked proso millet, and the adding amount of baijiu is 60% of the weight of the cooked proso millet;

(4) pressing the mash obtained in step (3) and filtering the pressed mash to obtain a wine liquid and a vinasse, allowing the wine liquid to stand for 3 days at 5° C. to obtain a supernatant, filtering the supernatant to prepare a raw wine, wherein a filter cloth made of nylon 36 is used in all of the above filtering;

(5) sterilizing the raw wine obtained in step (4) at 70° C. for 30 minutes, then aging for 3 years to produce an aged wine;

(6) adding pure water to the aged wine obtained in step (5) to adjust alcohol content to 21% by volume, then adding a white sugar to adjust sugar degree to 3°, finally adding a caramel pigment to adjust the color, thereby obtaining a semi-finished wine;

(7) filling the semi-finished wine of step (6) and sterilizing at 90° C. for 10 minutes, then packing and storing to make a health preserving wine.

Comparative Example 1

Provided is a health preserving wine, comprising the following parts by weight of raw materials:

9.0 parts by weight of Rhizoma Polygonati; 51.5 parts by weight of baijiu; 81.0 parts by weight of proso millet; 9.9 parts by weight of Daqu; and 0.01 parts by weight of yeast.

Also provided is a preparation method of a health preserving wine prepared by using the above raw materials, comprising the following steps:

(1) soaking 81.0 parts by weight of proso millet in water for 2.5 days, and then cooking at 83° C. for 20 minutes to obtain a cooked proso millet;

(2) cooling the cooked proso millet in step (1) to 25° C., then adding it to a fermentation tank, adding water and 9.9 parts by weight of daqu, 0.1 parts by weight of yeast and 9.0 parts by weight of Rhizoma Polygonati and 51.5 parts by weight of baijiu, fermenting at 28° C. for 4 days, then adding baijiu again, and further fermenting at 20° C. for 55 days to prepare a mash, wherein the adding amount of water is 2.5 times the weight of the cooked proso millet, and the adding amount of baijiu in the second time is 50% the weight of the cooked proso millet;

(3) pressing the mash obtained in step (2) to obtain a pressed mash, and filtering the pressed mash to obtain a wine liquid and a vinasse, allowing the wine liquid to stand for 2.5 days at 10° C. to obtain a supernatant, filtering the supernatant to prepare a raw wine, wherein a filter cloth made of nylon 36 is used in all of the above filtering;

(4) sterilizing the raw wine obtained in step (3) at 80° C. for 20 minutes, then aging for 2 years to produce an aged wine;

(5) adding pure water to the aged wine obtained in step (4) to adjust the alcohol content to 18% by volume, then adding a white sugar to adjust sugar degree to 6°, finally adding a caramel pigment to adjust the color, thereby obtaining a semi-finished wine;

(6) filling the semi-finished wine obtained step (5) and sterilizing at 80° C. for 20 minutes, then packing and storing to make a health preserving wine.

Comparative Example 2

Provided is a health preserving wine, comprising the following parts by weight of raw materials:

4.5 parts by weight of Rhizoma Polygonati; 4.5 parts by weight of *Astragalus membranaceus*; 81.0 parts by weight of proso millet; 9.9 parts by weight of daqu; and 0.1 parts by weight of yeast.

Also provided is a preparation method of a health preserving wine prepared by using the above raw materials, comprising the following steps:

(1) soaking 81.0 parts by weight of proso millet in water for 2.5 days, and then cooking at 83° C. for 20 minutes to obtain a cooked proso millet;

(2) cooling the cooked proso millet obtained in step (1) to 25° C., then adding it to a fermentation tank, adding water and 9.9 parts by weight of daqu, 0.1 parts by weight of yeast and 4.5 parts by weight of Rhizoma Polygonati, and 4.5 parts by weight of *Astragalus membranaceus*, fermenting at 28° C. for 4 days, then adding baijiu again, and further fermenting at 20° C. for 55 days to prepare a mash, wherein the adding amount of water is 2.5 times the weight of the cooked proso millet, and the adding amount of baijiu is 50% the weight of the cooked proso millet;

(3) pressing the mash obtained in step (2) to obtain a pressed mash and filtering the pressed mash to obtain a wine liquid and a vinasse, allowing the wine liquid to stand for 2.5 days at 10° C. to obtain a supernatant, filtering the supernatant to prepare a raw wine, wherein a filter cloth made of nylon 36 is used in all of the above filtering;

(4) sterilizing the raw wine obtained in step (3) at 80° C. for 20 minutes, then aging for 2 years to produce an aged wine;

(5) adding pure water to the aged wine obtained in step (4) to adjust the alcohol content to 18% by volume, then adding a white sugar to adjust sugar degree to 6°, finally adding a caramel pigment to adjust the color, thereby obtaining a semi-finished wine;

(6) filling the semi-finished wine obtained step (5) and sterilizing at 80° C. for 20 minutes, then packing and storing to make a health preserving wine.

Test Example 1

In order to further demonstrate the performance of the health preserving wine of the present application, the health preserving wine prepared in Examples 1-3 and Comparative Examples 1-2 of the present application are tested in the following experiments. Wine prepare with proso millet alone as raw material is set as a control group.

(1) Yield of Liquor and Taste

TABLE 1

Performance of the health preserving wine

| Number | components of raw materials (by weight) | Color | Yield of liquor | Alcohol content (v/v %) | feeling by taste |
|---|---|---|---|---|---|
| Control group | proso millet alone | light yellow | 200% | 21 | Rich aroma, sweet and mellow, unique flavor |
| Example 1 | Rhizoma Polygonati, 4.5 parts, Rhizoma Polygonati-soaked solution mixture, 56.0 parts, proso millet, 81.0 parts, Daqu, 9.9 parts, Yeast, 0.1 parts | light yellow | 192% | 21 | good balance of flavors, pure wine body and pleasant aroma |
| Example 2 | Rhizoma Polygonati, 2.5 parts Rhizoma Polygonati-soaked solution mixture, 27.5 parts proso millet, 85.0 parts Daqu, 9.9 parts yeast, 0.1 parts | light yellow | 195% | 15 | good balance of flavors, pure wine body and pleasant aroma |
| Example 3 | Rhizoma Polygonati, 6.5 parts Rhizoma Polygonati-soaked solution mixture, 84.5 parts proso millet, 77.0 parts Daqu; 9.9 parts yeast, 0.1 parts | light yellow | 187% | 19 | good balance of flavors, pure wine body and pleasant aroma |
| Comparative Example 1 | Rhizoma Polygonati; 9.0 parts baijiu, 51.5 parts proso millet, 81.0 parts; Daqu, 9.9 parts; yeast, 0.1 parts. | light yellow | 180% | 21 | good balance of flavors, pure wine body and pleasant aroma |
| Comparative Example 2 | Rhizoma Polygonati, 4.5 parts; Astragalus membranaceus, 4.5 parts, proso millet; 81.0 parts, daqu, 9.9 parts; yeast, 0.1 parts. | light yellow | 178% | 21 | good balance of flavors, pure wine body and pleasant aroma |

From Table 1, it can be concluded that in Examples 1-3 the yield of liquor was 187% to 200% (the amount of proso millet), and the alcohol content (v/v %) is 15 to 21% by volume. The yields of liquor of the comparative Examples 1 and 2 were 180% and 178% (the amount of proso millet) respectively, and the alcohol contents (v/v %) are both 21% by volume. The results indicate that the preparation method of the health preserving wine provided by the present application adopts the combination of fermentation and soaking process, and as a result, a new type of tonifying alcoholic beverage with good balance of flavors, pure wine body, pleasant aroma, low alcohol content and unique flavor is obtained. Besides, the yield of liquor is higher than that obtained by fermentation of Rhizoma Polygonati alone and that obtained by fermentation of Rhizoma Polygonati and *Astragalus membranaceus.*

(2) Dissolution Rate of Raw Material Components

The dissolution rate of the active ingredient of the main raw material Rhizoma Polygonati contained in the health preserving wine prepared in Examples 1-3 and Comparative Example 1-2 of the present application was examined by high performance liquid chromatography. The results showed that the dissolution rates of the main components of Rhizoma Polygonati in Examples 1-3 were 38.6%, 34.8%, and 35.9%, respectively. The dissolution rates of the main components of Rhizoma Polygonati in Comparative Examples 1-2 were 21.8% and 20.9%, respectively.

The above test results showed that, through the combination of fermentation and soaking process, the active ingredients of Rhizoma Polygonati are dissolved into the wine liquid due to soaking as well as fermentation, so that the dissolution rate of the active ingredient of Rhizoma Polygonati is greatly improved. The contents of the effective ingredients of Rhizoma Polygonati are increased, so that the efficacy of Rhizoma Polygonati is maximized, and the health preserving effect of the health preserving wine is strengthened.

(3) Tests of Health Preserving Effect

1. Subhealthy Population Observation

The health preserving effect of the wine prepared from proso millet alone and the health preserving wines prepared in Examples 1-3 and comparative Examples 1-2 were respectively tested in 100 people with low immunity and fatigue (taking twice a day, once in the morning and once in the evening, 50 mL each time). The results showed that after three months of continuous use, people who took the wine prepared from proso millet alone showed no obvious effects. The fatigue of 82 or more people who took the wine prepared in Examples 1-3 and Comparative Example 2 was significantly reduced (no statistical difference therebetween), and the level of the fatigue improvement was significantly better than that of the 82 or more people who took the health preserving wine prepared in Comparative Example 1, but the 16 people who took the health preserving wine prepared in Comparative Example 2 felt discomfort and showed symptoms of developing slight inflammatory.

The above test results show that the health preserving wine prepared by the fermentation and the soaking process according to the present application has obvious health preserving effects for improving the body's immune function and nourishing and strengthening the body, and the health preserving effect of the health preserving wine of the present application is superior to that of the health preserving wine prepared by simple fermentation of Rhizoma Polygonati, and no less than that of the health preserving wine made by fermentation of Rhizoma Polygonati and *Astragalus membranaceus*.

2. Animal Experiments

Experimental Animal

BALB/c mice, weighing 20-24 g, provided by Beijing Huafukang Biotechnology Co., Ltd. Certificate No. SCXK (Beijing) 2009-0004.

Experimental Method (1) Animal grouping and treatment method: 50 mice were randomly divided into 5 groups, which were normal control group, model group, group of wine prepared from proso millet alone, group of health preserving wine of examples 1-3 and group of health preserving wine of comparative examples 1-2, respectively. The normal control group was given quantitative water and food supply, and other groups were injected subcutaneously with hydrocortisone 50 mg/kg once daily for 6 days, constructing a low immune function model. On the 7th day, the group of wine prepared from proso millet alone, group of health preserving wine of examples 1-3 and group of health preserving wine of comparative examples 1-2 were given the corresponding health preserving wine once a day for 7 consecutive days, 0.4 mL each time. The model group was given distilled water of equal volume for 7 consecutive days.

(2) Immunological function test: each mouse of the above groups was intraperitoneally injected with 0.2 mL/10 g body weight of chicken erythrocyte suspension. After 30 min, 1 mL/10 g body weight of Hank's solution was intraperitoneally injected. After 2 minutes, the mice were executed by cervical dislocation, and peritoneal lavage fluid was dripped on the center of a slide, and spread out properly to obtain a sample. The sample was placed in a wet box containing ice cubes, and after 60 minutes, rinsed with 0.9% NaCl to remove non-adherent cells, then quickly rinsed twice with distilled water, then immediately rinsed in 0.9% NaCl to restore osmotic pressure, then air dried, and stained by Wright-Gemsa, and counted under oil microscope for 200 macrophages, in which the number of macrophages and the number of chicken red blood cells phagocytosed were recorded, and the percentage of phagocytosis and phagocytic index were calculated.

Percentage of phagocytosis=number of macrophages that wallow chicken red blood cells/200 macrophages×100%.

Phagocytic index=number of chicken red blood cells swallowed by 200 macrophages/200 macrophages.

(3) Statistical methods: Data analysis was performed using SPSS 17.0 statistical software, and the results were expressed by ±s. One-way ANOVA was used to compare the average values between groups, wherein P<0.05 indicates that the difference was statistically significant.

(4) Results

Effects of wine prepared from proso millet alone, health preserving wines prepared in Examples 1-3 and comparative Examples 1-2 on phagocytosis function of mouse peritoneal macrophages.

Compared with the model group, the group of wine prepared from proso millet didn't show obvious effects. The phagocytic index and the percentage of phagocytosis of the peritoneal macrophages of the mice in the group of health preserving wine of examples 1-3 and group of health preserving wine of comparative example 2 were significantly increased. The difference was statistically significant. The phagocytosis index and the percentage of phagocytosis of the peritoneal macrophages of the mice in the group of health preserving wine of comparative example 1 had an tendency to increase, but the difference was not statistically significant. Compared with the normal group, there was no significant difference in the phagocytosis index and the percentage of phagocytosis of the peritoneal macrophage of the mice in the group of health preserving wine of examples 1-3 and comparative example 2, but the phagocytosis index and the percentage of phagocytosis of the peritoneal macrophage of the mice in the group of wine prepared from proso millet and group of health preserving wine of comparative example 1 were both decreased. See Table 2.

TABLE 2

Effect of a health preserving wine of Rhizoma Polygonation phagocytosis of mouse peritoneal macrophages ($\overline{X} \pm s$, n = 10)

| Groups | percentage of phagocytosis | phagocytosis index |
|---|---|---|
| normal control group | 32.69 ± 5.43 | 0.92 ± 0.07 |
| model group | 18.11 ± 4.50 | 0.53 ± 0.08 |
| group of wine prepared from proso millet alone | 19.38 ± 4.82# | 0.54 ± 0.06# |
| group of health preserving wine of example 1 | 29.75 ± 5.73* | 0.88 ± 0.09* |
| group of health preserving wine of example 2 | 31.96 ± 6.18* | 0.90 ± 0.11* |
| group of health preserving wine of example 3 | 28.87 ± 5.24* | 0.88 ± 0.10* |
| group of health preserving wine of comparative example 1 | 22.34 ± 5.01# | 0.57 ± 0.05# |
| group of health preserving wine of comparative example 2 | 29.13 ± 5.32* | 0.87 ± 0.09* |

Note:
compared with the model group, *P < 0.05;
compared with the normal group, #P < 0.05.

(5) Conclusion

After testing, the results showed that the health preserving wine prepared in examples 1-3 can play a positive regulatory role in the immune system of immunocompromised mice, and its regulation effect is significantly better than that of the health preserving wine prepared in Comparative Example 1, and is no less than that of the health preserving wine prepared in Comparative Example 2.

(4) Test of Hygienic Standard GB2758-81

The health preserving wines prepared in Examples 1-3 of the present application were tested according to the hygienic standard GB 2758-81, and the results were as follows:

1. Organoleptic index: clear liquid, no precipitation and impurities, no foreign odor and off-flavor.

2. Physical and chemical indicators:

| Item | indicator |
|---|---|
| Amount of the residual sulfur dioxide (g/kg, based on free $SO_2$) | ≤0.05 |
| aflatoxin $B_1$ (μg/kg) | ≤5 |

3. Bacterial indicators:

| Item | standard |
|---|---|
| Total number of bacteria (number/mg) | ≤50 |
| Coliforms (number/100 ml) | ≤3 |

The test results showed that the health preserving wine prepared by present application fully meets the requirements of GB2758-81 standard.

Obviously, the above mentioned examples are merely made to clearly illustrate the present application and are not intended to limit the embodiments. Other variations or modifications of different forms may be made by those skilled in the art based on the above description. There is no need and no way to exhaust all the embodiments. Obvious variations or modifications resulting therefrom are still within the scope of the present application.

The invention claimed is:

1. A method for preparing a health preserving wine, comprising the following steps:
    (1) soaking 2.5 to 6.5 parts by weight of Rhizoma Polygonati in 25.0 to 78.0 parts by weight of baijiu to obtain 27.5 to 84.5 parts by weight of a Rhizoma Polygonati-soaked solution mixture which is a mixture of a baijiu soaking solution of Rhizoma Polygonati and dregs, wherein baijiu has an alcohol content by volume of 55% to 65%;
    (2) subjecting 77.0 to 85.0 parts by weight of proso millet to soaking and cooking to obtain a cooked proso millet;
    (3) cooling the cooked proso millet obtained in step (2) at a temperature of 24 to 26° C. to obtain a cooled proso millet, then adding the cooled proso millet to a fermentation tank, adding water and 9.9 parts by weight of daqu, 0.1 parts by weight of yeast and 2.5 to 6.5 parts by weight of Rhizoma Polygonati, fermenting at 25° C. to 30° C. for 3 to 5 days, then adding baijiu and 27.5 to 84.5 parts by weight of the Rhizoma Polygonati-soaked solution mixture obtained in step (1), and further fermenting at 18° C. to 22° C. for 50 to 60 days to prepare a mash;
    (4) pressing the mash obtained in step (3) to obtain a pressed mash, separating the pressed mash to obtain a wine liquid and a vinasse, allowing the wine liquid to stand for 2 to 3 days at 5° C. to 15° C. to obtain a supernatant, filtering the supernatant to prepare a raw wine;
    (5) sterilizing the raw wine obtained in step (4) at 70° C. to 90° C. for 10 to 30 minutes, then aging for at least 1 year to produce an aged wine;
    (6) adding pure water to the aged wine obtained in step (5) to adjust alcohol content to 15% to 21% by volume, then adding a white sugar and/or a crystal sugar to adjust sugar degree to 3 to 10°, finally adding a caramel pigment to adjust the color, thereby obtaining a semi-finished wine;
    (7) bottling the semi-finished wine obtained in step (6) in a bottle and sterilizing the bottle at 70° C. to 90° C. for 10 to 30 minutes, then packing and storing the bottle to make a health preserving wine.

2. The method according to claim 1, wherein the soaking in step (1) is carried out at a temperature of 10° C. to 25° C.

3. The method according to claim 1, wherein the cooked proso millet in step (2) is obtained by: soaking the proso millet in water for 2 to 3 days, and cooking for 15 to 25 minutes at a temperature of 75° C. to 90° C.

4. The method according to claim 1, wherein in step (3) said adding water comprises adding water in an amount of 2 to 3 times a weight of the cooked proso millet, and said adding baijiu comprises adding baijiu in an amount of 40% to 60% of the weight of the cooked proso millet.

5. The method according to claim 1, wherein in step (4) said filtering the pressed mash is carried out with a filter cloth made of nylon 36, and said filtering the supernatant is carried out with a filter cloth made of nylon 36.

6. The method according to claim 2, wherein in step (3) said adding water comprises adding water in an amount of 2 to 3 times a weight of the cooked proso millet, and said adding baijiu comprises adding baijiu in an amount of 40% to 60% of the weight of the cooked proso millet.

7. The method according to claim 2, wherein in step (4) said filtering the pressed mash is carried out with a filter cloth made of nylon 36, and said filtering the supernatant is carried out with a filter cloth made of nylon 36.

* * * * *